United States Patent
Hashimshony et al.

(10) Patent No.: US 9,901,362 B2
(45) Date of Patent: Feb. 27, 2018

(54) MEDICAL DEVICE AND METHOD FOR USE IN TISSUE CHARACTERIZATION AND TREATMENT

(71) Applicant: DUNE MEDICAL DEVICES LTD., Caesarea (IL)

(72) Inventors: Dan Hashimshony, Givat Ada (IL); Gil Cohen, Jerusalem (IL)

(73) Assignee: DUNE MEDICAL DEVICES LTD., Caesarea (IL)

( * ) Notice: Subject to any disclaimer, the term of this patent is extended or adjusted under 35 U.S.C. 154(b) by 639 days.

(21) Appl. No.: 13/676,993

(22) Filed: Nov. 14, 2012

(65) Prior Publication Data

US 2013/0072815 A1    Mar. 21, 2013

Related U.S. Application Data

(63) Continuation-in-part of application No. 12/663,923, filed as application No. PCT/IL2008/000965 on Jul. 13, 2008, now Pat. No. 9,301,734.

(Continued)

(51) Int. Cl.
*A61B 17/00* (2006.01)
*A61B 18/14* (2006.01)
(Continued)

(52) U.S. Cl.
CPC ........ *A61B 17/3205* (2013.01); *A61B 5/6847* (2013.01); *A61B 5/743* (2013.01);
(Continued)

(58) Field of Classification Search
CPC ............ A61B 10/0275; A61B 17/3205; A61B 2017/00057; A61B 2017/00039; A61B 2017/00026
See application file for complete search history.

(56) References Cited

U.S. PATENT DOCUMENTS 3,910,279 A    10/1975   Okada et al.
5,630,426 A     5/1997   Eggers et al.
(Continued)

FOREIGN PATENT DOCUMENTS

JP    2003520062 A    7/2003
JP    2008165680 A    7/2008
(Continued)

OTHER PUBLICATIONS

Nov. 25, 2011 Office Action issued in European Patent Application No. 08 776 603.6.
(Continued)

*Primary Examiner* — Sean Dougherty
(74) *Attorney, Agent, or Firm* — Browdy and Neimark, PLLC (57) ABSTRACT

A medical device is presented for use in tissue characterization and treatment. The device comprises: a tissue characterization probe comprising an elongated carrier for carrying an array of tissue characterization sensors arranged in a spaced-apart relationship at least along an axis of said carrier, such that progression of the probe through a tissue mass provides for locating and determining a dimension of an abnormal tissue specimen inside said tissue mass based on characterization signals from the sensors in the array, thereby enabling consequent treatment of the abnormal tissue specimen by a treatment tool.

25 Claims, 8 Drawing Sheets
(4 of 8 Drawing Sheet(s) Filed in Color)

Related U.S. Application Data (60) Provisional application No. 60/950,081, filed on Jul. 16, 2007.

(51) Int. Cl.
| | | |
|---|---|---|
| *A61B 19/00* | (2006.01) | |
| *A61B 17/3205* | (2006.01) | |
| *A61B 10/02* | (2006.01) | |
| *A61B 5/00* | (2006.01) | |
| A61B 5/053 | (2006.01) | |
| A61B 5/05 | (2006.01) | |

(52) U.S. Cl.
CPC ...... *A61B 10/0233* (2013.01); *A61B 10/0266* (2013.01); *A61B 10/0275* (2013.01); *A61B 17/32056* (2013.01); *A61B 5/0084* (2013.01); *A61B 5/053* (2013.01); *A61B 5/0507* (2013.01); *A61B 5/4836* (2013.01); *A61B 2562/043* (2013.01)

(56) References Cited

U.S. PATENT DOCUMENTS

| | | | |
|---|---|---|---|
| 5,800,350 A * | 9/1998 | Coppleson | A61B 5/0059 600/372 |
| 5,846,513 A | 12/1998 | Carroll et al. | |
| 6,006,755 A | 12/1999 | Edwards | |
| 6,022,362 A | 2/2000 | Lee et al. | |
| 6,120,437 A | 9/2000 | Yoon et al. | |
| 6,321,109 B2 | 11/2001 | Ben-Haim et al. | |
| 6,331,166 B1 | 12/2001 | Burbank et al. | |
| 6,419,635 B1 | 7/2002 | Hedengren et al. | |
| 6,419,640 B1 | 7/2002 | Taylor | |
| 6,440,147 B1 * | 8/2002 | Lee et al. | 606/159 |
| 6,689,145 B2 | 2/2004 | Lee et al. | |
| 6,780,179 B2 | 8/2004 | Lee et al. | |
| 6,813,515 B2 | 11/2004 | Hashimshony | |
| 7,101,378 B2 | 9/2006 | Salameh et al. | |
| 7,122,011 B2 | 10/2006 | Clifford et al. | |
| 7,184,824 B2 | 2/2007 | Hashimshony | |
| 8,413,582 B1 | 4/2013 | Chen | |
| 2001/0047169 A1 | 11/2001 | McGuckin, Jr. et al. | |
| 2001/0056236 A1 * | 12/2001 | Angelsen | A61B 8/06 600/458 |
| 2002/0019597 A1 | 2/2002 | Dubrul et al. | |
| 2002/0035361 A1 | 3/2002 | Houser et al. | |
| 2003/0009110 A1 * | 1/2003 | Tu et al. | 600/547 |
| 2003/0050574 A1 | 3/2003 | Krueger | |
| 2003/0055423 A1 | 3/2003 | Levinson | |
| 2003/0138378 A1 | 7/2003 | Hashimshony | |
| 2004/0243018 A1 | 12/2004 | Organ et al. | |
| 2004/0255739 A1 | 12/2004 | Clifford et al. | |
| 2005/0203419 A1 | 9/2005 | Ramanujam et al. | |
| 2006/0235286 A1 | 10/2006 | Stone et al. | |
| 2006/0270942 A1 * | 11/2006 | McAdams | A61B 5/0531 600/547 |
| 2008/0039742 A1 | 2/2008 | Hashimshony et al. | |
| 2008/0214955 A1 | 9/2008 | Speeg et al. | |
| 2008/0287750 A1 | 11/2008 | Hashimshony et al. | |
| 2010/0168611 A1 | 7/2010 | Hashimshony et al. | |
| 2011/0034806 A1 | 2/2011 | Hartov et al. | |
| 2012/0316463 A1 | 12/2012 | Hashimshony et al. | |
| 2012/0323134 A1 | 12/2012 | Cory et al. | |
| 2013/0177972 A1 * | 7/2013 | Green et al. | 435/288.7 |
| 2013/0267821 A1 | 10/2013 | Hashimshony et al. | |

FOREIGN PATENT DOCUMENTS

| | | |
|---|---|---|
| JP | 2009136377 A | 6/2009 |
| JP | 2009526554 A | 7/2009 |
| JP | 2010512848 A | 4/2010 |
| WO | WO 92/17108 A1 | 10/1992 |
| WO | WO 98/12968 | 4/1998 |
| WO | WO 99/44506 A1 | 9/1999 |
| WO | 0069335 A1 | 11/2000 |
| WO | WO 01/74252 A2 | 10/2001 |
| WO | WO 01/82998 A2 | 11/2001 |
| WO | WO 2006/103665 A2 | 10/2006 |
| WO | WO 2007/015255 A2 | 2/2007 |
| WO | WO 2007/083310 A2 | 7/2007 |
| WO | 2007149595 A2 | 12/2007 |
| WO | 2008076712 A2 | 6/2008 |
| WO | 2009/4310960 A2 | 1/2009 |
| WO | WO 2011/016035 A1 | 2/2011 |
| WO | 2012/092016 A1 | 7/2012 |

OTHER PUBLICATIONS

Mar. 23, 2009 International Search Report and Written Opinion issued in International Application No. PCT/IL2008/000965.

* cited by examiner

MEDICAL DEVICE AND METHOD FOR USE IN TISSUE CHARACTERIZATION AND TREATMENT

CROSS-REFERENCE TO RELATED APPLICATIONS

This is a new U.S. Continuation-in-Part Application of prior pending U.S. application Ser. No. 12/663,923, filed Dec. 10, 2009, which claims priority from PCT Application No. PCT/IL08/00965 filed Jul. 13, 2008 and Provisional U.S. Patent Application No. 60/950,081 filed on Jul. 16, 2007. The disclosure of each of the prior applications is hereby incorporated herein by reference in its entirety.

FIELD OF THE INVENTION

This invention relates to medical devices and methods for use in tissue characterization and treatment.

BACKGROUND

Techniques for in situ identifying abnormal (e.g. tumorous) cells in a biological tissue are generally known. Such techniques include those utilizing determination of the electrical properties of a tissue, for example, by determination of electrical impedance or dielectric constants. Some kinds of tumors can be identified by determining differences in the measured electrical properties of the tissue. The identified and located region of abnormal tissue can then be treated and/or removed from the body Various types of tissue characterization sensor and its integration with a tissue treatment/removal tool are described in the following patent publications, all assigned to the assignee of the present application: US2003138378, WO2006103665, WO2007015255, U.S. Pat. No. 6,813,515 and U.S. Pat. No. 7,184,824.

Also, various techniques are known for removing a certain tissue specimen from a tissue mass. These techniques are disclosed for example in U.S. Pat. No. 6,689,145 and U.S. Pat. No. 7,122,011.

General Description

There is a need in the art to facilitate precise location and determination of a volume of a tissue specimen (e.g. abnormal tissues) to be treated (e.g. removed). Also, there is need in the art for a tissue treatment technique capable of adjusting a treatment volume to the determined volume of the abnormal tissue specimen.

The present invention solves the above problems by providing a novel medical device for use in tissue characterization and treatment. The device comprises a tissue characterization probe comprising an elongated carrier for carrying an array of tissue characterization sensors arranged in a predetermined spaced-apart relationship at least along an axis of said carrier. During the progression of the probe through a tissue mass, signals from the tissue characterization sensors are used for locating and determining a dimension of an abnormal tissue specimen inside the tissue mass. This enables consequent treatment of the abnormal tissue specimen by a treatment tool.

In preferred embodiment of the invention, the treatment tool is mounted on the characterization probe carrier. The treatment tool may be configured for carrying out at least one of the following biopsy, cutting, delivering physical treatment, delivering treatment medication, diagnostics.

Preferably, the treatment tool is selectively shiftable between its inoperative position being located substantially entirely inside the carrier and its operative position projecting by its at least one tissue treating portion towards outside the carrier. In preferred embodiments of the invention, the dimension of the tissue treating portion(s) projectable from the carrier, and possibly also location of the tissue treating portion(s) with respect to the carrier can be controllably varied.

In some embodiments of the invention, the probe carrier is formed with a guiding cutting tool, to facilitate insertion of the probe to a targeted location in the tissue. Also, in some embodiments of the invention, a marker may be left in the body, at the location of the treated (removed) tissue.

The invention also provides a novel method for use in tissue characterization and treatment. A tissue mass is scanned with an array of tissue characterization sensors arranged in a predetermined spaced-apart relationship along a scanning axis, and signals from the sensors are detected and analyzed while scanning locate and determine a dimension of an abnormal tissue specimen inside said tissue mass that is to be treated during progression of the array through the tissue mass.

Additionally, the invention provides a system for use in tissue characterization and treatment. The system comprises a medical device and a control unit connectable to the medical device. The latter is configured as described above, namely comprises a tissue characterization probe having a carrier on which an array of tissue characterization sensors is mounted with the sensors being arranged in a spaced-apart relationship at least along an elongated axis of the carrier. The control unit is configured for receiving and analyzing tissue characterizing signals from each of all the sensors and utilizing data indicative of the respective sensors' location, for determining a dimension of an abnormal tissue specimen.

The present invention further provides for a novel convenient presentation of the measurement results. As indicated above, the tissue characterization probe of the invention includes an array (one- or two-dimensional array) of tissue characterization sensors. In the simplest example, this is a one-dimensional array of spaced-apart sensors along the longitudinal axis of the probe. Thus, for a given position of the probe with respect to tissue under measurements, the array of sensors arranged in a predetermined fashion actually presents an array of measurement locations/sites. According to the invention, such an array/matrix of the measurement locations (sensors' positions) is displayed together with corresponding measured data.

According to another aspect of the invention, there is provided a system for use in tissue characterization and treatment, the system comprising the above described medical device and a control unit connectable thereto. The control unit comprises a graphical user interface configured for presenting information related to the signals received from all the sensors, thereby providing an operator with information regarding the tissue type at the locations of the sensors, and facilitating analysis of the location and extent of the tissue to be treated.

According to yet another aspect of the invention, there is provided a control unit for monitoring measurements of tissue properties, the control unit comprising a graphical user interface configured for presenting information related to signals received from an array of sensors arranged in a predetermined spaced-apart relationship along a measurement axis, the presented information being in the form of an array of locations spaced-apart along an axis corresponding to the array of said sensors, and a corresponding array of measured data in association with the array of said locations, said array of measured data being indicative of signals received from the array of the sensors respectively, thereby providing an operator with information regarding a profile of a measured tissue profile along a tissue mass aligned with the array of sensors.

According to yet further aspect of the invention, there is provided a graphical user interface configured for presenting information related to signals received from an array of sensors arranged in a predetermined spaced-apart relationship along a measurement axis, the presented information being in the form of an array of locations spaced-apart along an axis corresponding to the array of said sensors, and a corresponding array of measured data in association with the array of said locations, said array of measured data being indicative of signals received from the array of the sensors respectively, thereby providing an operator with information regarding a profile of measured tissue properties along a tissue mass aligned with the array of sensors.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
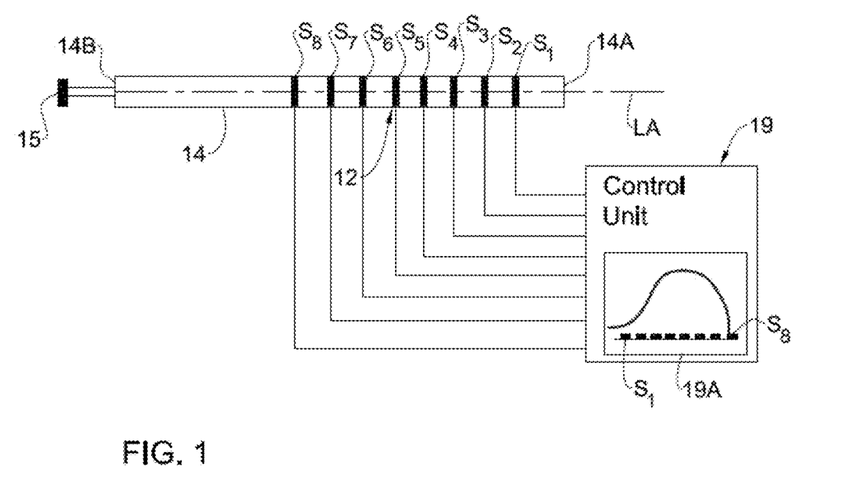
FIG. 1 is a schematic illustration of a medical device of the present invention.

Referring to FIG. 1, there is schematically illustrated a medical device, generally designated 10, according to an embodiment of the invention. The device 10 is configured for use in tissue characterization and treatment, and includes a tissue characterization probe 12 carried by an elongated shaft 14, which has distal and proximal ends 14A and 14B, respectively, and is formed with a control handle 15 at its proximal end 14B. The tissue characterization probe 12 includes an array of tissue characterization sensors, eight such sensors $S_1$-$S_8$ being shown in the present example.

The tissue characterization sensor array may include one or more of optical, radiofrequency (RF), microwave (MW), electrical, magnetic, temperature, elastic, biological, chemical, radioactive-emission, and mechanical sensors of any known type. The construction and operation of the tissue characterization sensor does not form part of the present invention, and therefore need not be specifically described. For example, sensors described in the above indicated patent publications assigned to the assignee of the present application may be used.

The sensors $S_1$-$S_8$ are arranged in a spaced-apart relationship along a longitudinal axis LA of the carrier 14, and may be arranged in one- or two dimensional array. For example, the sensor array may include, in addition to a group of sensors arranged in one-dimensional array, sensors arranged in a spaced-apart manner along a circumferential region of the carrier. The sensor array gives, in real time, indication about the nature of tissue along the carrier 14.

The sensors are spaced along the axis LA from one another a known distance, which may or may not be equal for all the sensors in the array. The known relative locations of the sensors along the carrier 12 allows for identifying corresponding locations in a tissue mass when the probe is progressing through the tissue mass (i.e. scans the tissue) based on signals received from the sensors. In this connection, the medical device 10 is associated with an appropriate control system 19 configured for receiving and analyzing the signals generated by the sensors. It should be understood that connection between the sensors and the control unit is shown in the figure schematically, and in case wired connection is used such wires would extend inside the shaft 14 and exit at the proximal end 14B.

The control system may be an external system connectable (via wires or wireless signal transmission) to the sensors, or may be a constructional part of the probe itself. The control system, based on the analysis of the received signals, operates for determining a location of the margins of an abnormal tissue region inside the examined tissue mass and generating output data indicative of a dimension of the abnormal tissue region. This allows for consequent treatment of the abnormal tissue region by an appropriate treatment tool.

The control system preferably includes a graphical user interface (GUI) 19A, and is configured for presenting information related to the signals received from each of the sensors. This information provides the operator with information regarding the tissue type at the locations of the sensors. For example, this may be presented as values of one or multiple parameters of the tissue at the multiple locations corresponding to the positions of the array of the sensors, at a given position of the probe with respect to the tissue. The tissue parameters may relate to the tissue type, physical tissue properties such as conductivity, permittivity, temperature, and others. The information presented on the GUI may assist the operator in analyzing the location and extent of the tissue to be treated. In the present example, GUI 19A displays the information in the form of a continuous graph/profile of a certain tissue property formed by values measured by all sensors. Other ways of presentation are also possible, and will be exemplified below with reference to FIGS. 7-14.

Generally, the treatment tool may be configured for carrying out one or more of the following: biopsy, cutting, delivering physical treatment, delivering treatment medication, diagnostics. More specifically, the present invention is used for removal of an intact tissue specimen (abnormal tissue) and is therefore described below with respect to this specific but not limiting example.

Preferably, the probe 12 also carries a treatment tool, e.g. a cutting tool. This is implemented by configuring the probe such that the treatment tool can be selectively shiftable between its inoperative position, when it is located substantially entirely inside the carrier 14, and its operative positions when its one or more excision elements (constituting one or more tissue treating elements) project(s) from the carrier.

In some examples of the invention, the selective projection of the excision element is achieved by using the treatment tool of a kind known in the art, where the excision element projects from the carrier body through an opening made along the body portion while moving with respect to the carrier along an axis inclines with respect to the axis LA. In some other examples, the excision element projects from the carrier (e.g. from its distal end) while moving with respect to the carrier substantially along the axis LA. Such configurations are also generally known in the art. The treatment tool may be configured with a removed tissue collecting unit, which may or may not be selectively projectable from the probe.

According to the invention, the medical device is configured such that a dimension of the excision element part projecting from the carrier can be controllably adjusted (varied) in accordance with the determined dimension of the abnormal tissue margins, thereby adjusting the excision volume. Preferably, the excision element is configured for both cutting the tissue and collecting the tissue being cut.

The following are some specific but not limiting examples of the configuration of the device of the present invention. The same reference numbers are used for identifying components that are common in all the examples.

Figure 2:
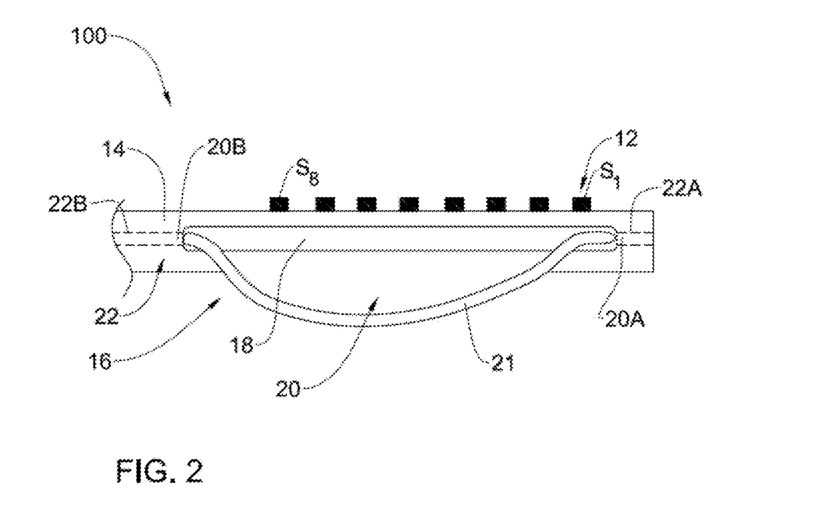
FIGS. 2 to 6 show five examples, respectively, of the device configuration for both the tissue characterization and removal of a tissue specimen.

FIG. 2 shows a medical device 100 for removal of an intact tissue specimen. The device 100 includes an elongated shaft/carrier 14 on which sensors $S_1$-$S_8$ of a tissue characterization probe 12 are mounted in spaced-apart locations, and a tissue cutting tool (generally, a treatment tool) 16 mounted on the carrier 14.

The cutting tool 16 has a body portion 22 located inside the carrier 14, and an excision element 20 projectable from the body 22 through an opening 18 made in the carrier 14 In the figure, the excision element 20 is shown in its operative projecting state. The excision element has a cutting edge 21, and may be configured to have a cup-like shape when in the projecting state, thereby enabling collection of tissue while being cut during the rotation of the carrier 14 and thus of the excision element 20.

The excision element 20 extends between its first and second ends 20A and 20B which are attached to respective first and second locations on the treatment tool body 22 and spaced-apart along the axis LA of the carrier 14. The treatment tool is configured to enable a controllable change of the dimensions of the excision element 20. In the present example, this is implemented by making the treatment tool body 22 from two spaced members 22A and 22B, where at least one of them is slidable with respect to the other along the carrier axis LA. As a result, a distance between the first and second locations, and accordingly the first and second ends 20A and 20B of the excision element, changes, thereby enable adjustment of the dimension of the cutting portion 21 projecting through the carrier 14.

By controlling the location of the excision element distal and proximal ends 20A and 20B along the carrier 14, and thus controlling the excision volume, a user can perform optimal removal of a tissue specimen, for example during a breast biopsy procedure. The entire excision element 20 may be movable along the body 22. Thus, the excision volume is controlled by user by changing the location of the excision element 20 along the carrier 14 and changing a distance between the distal and proximal ends of the excision element.

Figure 3:
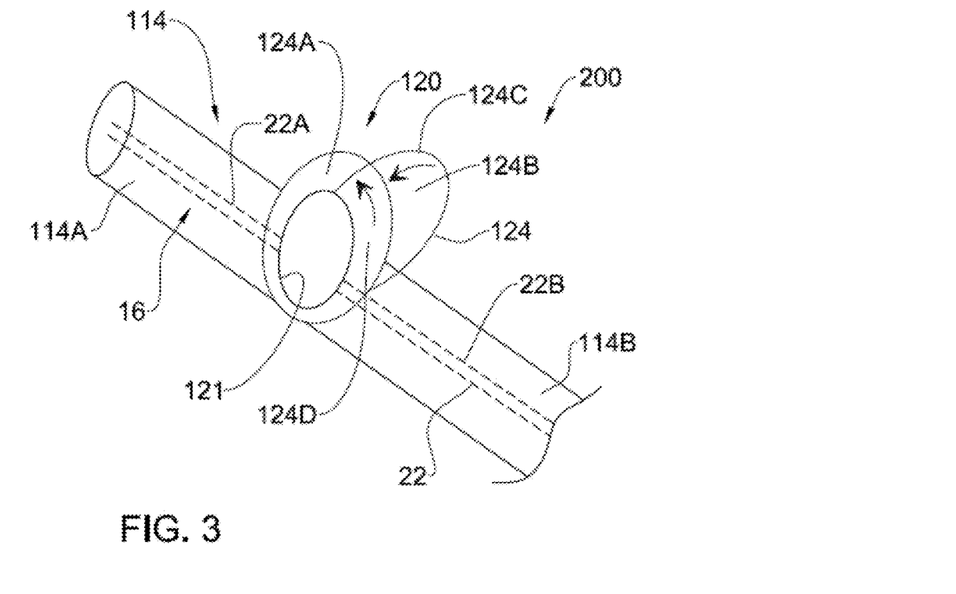

In the above example, the tissue removal procedure is carried while rotating the carrier 14. Such procedure can be performed while keeping the carrier position and rotating the treatment tool. This is exemplified in FIG. 3. A device 200 includes a carrier 114 formed by two separate parts 114A and 114B kept together by a treatment tool 16 inside the carrier 114. The treatment tool 16 has a body part 22 formed by two spaced-apart members 22A and 22B, and an excision element 120 attached thereto by its distal and proximal ends 20A and 20B. The excision element 120 has a semi-spherical surface 124 defining a cutting edge 21. The surface 124 has two arc-like portions 124A and 124B movable along the axis LA such that when they move towards one another one of the portions 124A becomes received by the other portion 124B. Also, the surface 124 has two parts 124C and 124D separately movable such that portion 124C can be received by portion 124C. These movements allow for altering the excision volume when in the operative projecting state of the excision element 120 and for shifting the element 120 between its operative projecting position and its inoperative position being located inside the carrier 14. Cutting is implemented while rotating the tool body 22 with respect to the carrier 14. Also, this configuration allows for collecting the tissue specimen while being cut.

Figure 4:
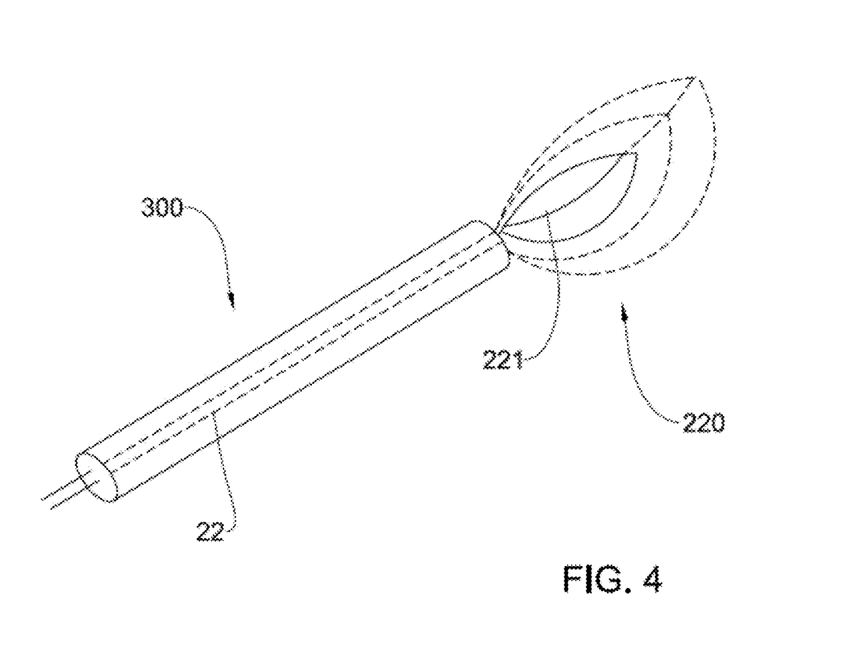

FIG. 4 shows a medical device 300 according to yet another example of the invention. Here, a treatment tool 216 has a body shaft 22 carrying at its distal end an excision element 220. The latter may or may not be integral with the body shaft 22. The excision element has a closed-loop cutting edge 221 which is pre-bent at fabrication so as to deploy from its inoperative closed position when inside the carrier 14 into an open ring-like shape when being projected from the carrier. Attached to the cutting edge 221 is a flexible tissue collecting unit. When the excision element is pushed (by user) out of the carrier 14 through its distal end, it gradually passes through its different operative states being of a spoon-like shape of different dimensions.

Figure 5:
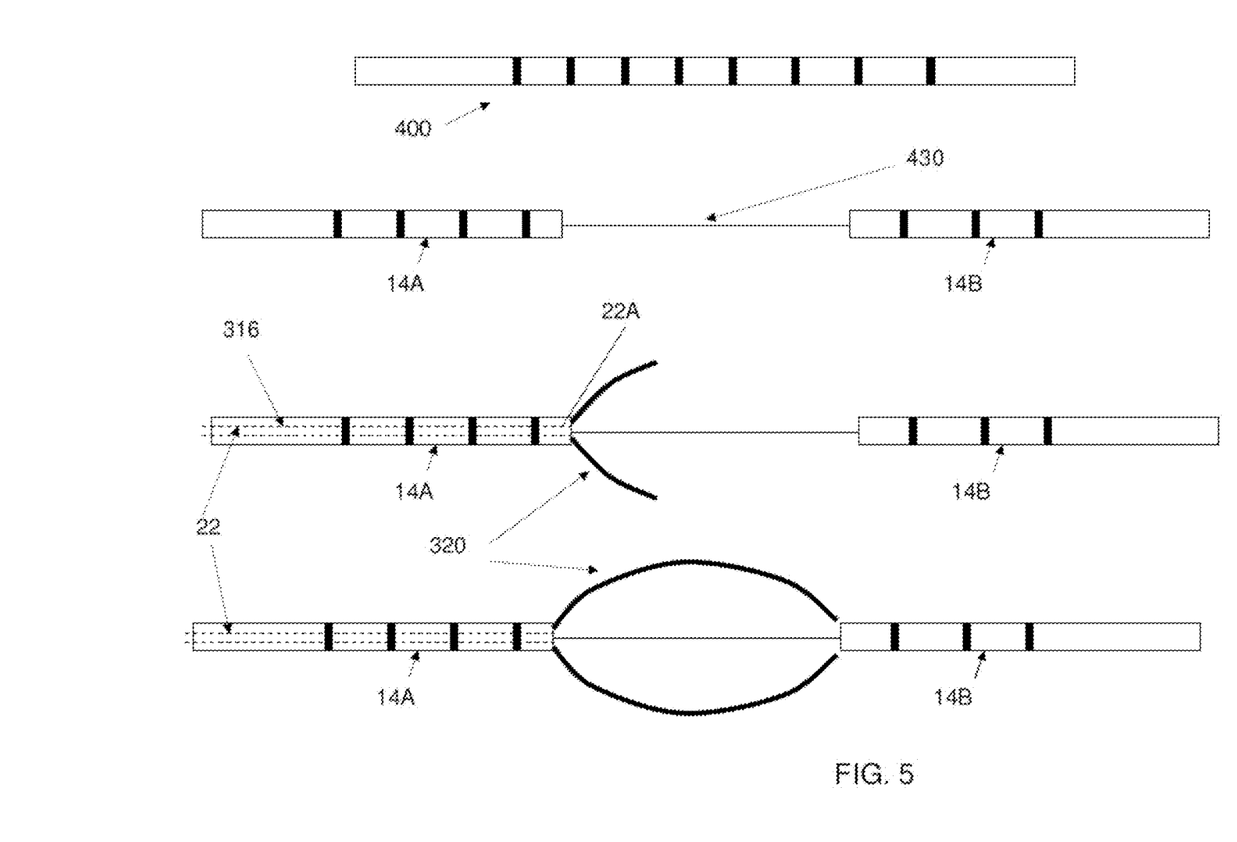

FIG. 5 shows a medical device 400 according to yet another example of the invention. Here, an elongated shaft (carrier) 14 is separable into two sections 14a and 14b, which remain connected to each other by a wire or shaft 430. A treatment tool 316 located inside the carrier 14 has a body shaft 22 carrying at its distal end 22A excision elements 320. The latter may or may not be integral with the body shaft 22. The treatment tool shaft 22 is advanced inside the shaft 14 until its distal end 22A reaches the distal end of the section 14A. Excision elements 220 are then deployed so as to excise an intact tissue portion.

Figure 6:
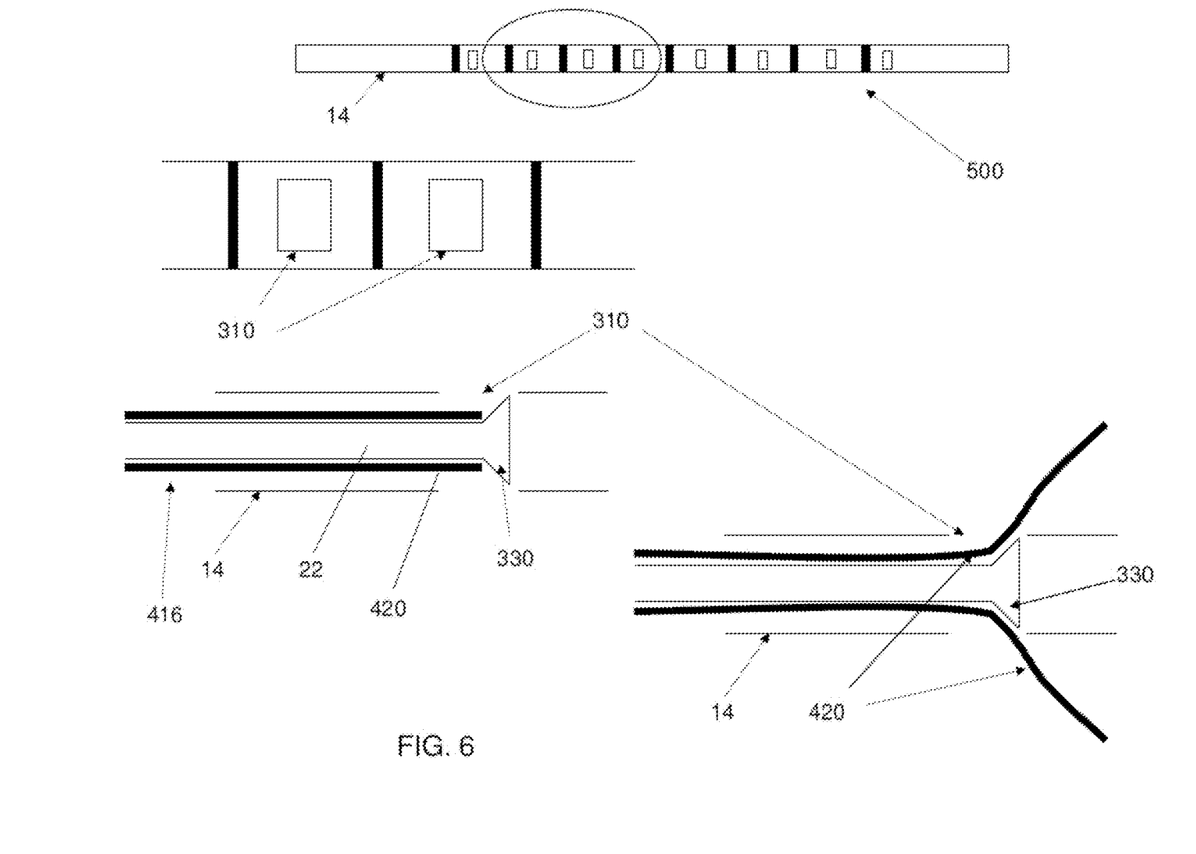

FIG. 6 shows a medical device 500 according to yet another example of the invention. Here, peripheral slots 310 are provided in the shaft/carrier 14 being interspaced between tissue characterization sensors. At each location along the shaft 14 there may be 2-8 peripheral slots. A treatment tool 416 has a body shaft 22 carrying at its distal end excision elements 420. The latter may or may not be integral with the body shaft 22. A number of excision elements 320 corresponds to the number of the slots 310. The treatment tool 416 is advanced inside the shaft 14 until its distal end is positioned at a specific slot 310 location. The distal end of the treatment tool shaft 22 has a tapered/angled ending portion 330. This ending portion allows for controlling an angle at which the excision elements 420 is extended from the shaft 14 into tissue. The excision elements 420 are pre-bent so that when extended they close back on the shaft 14, thus cutting the tissue portion adjacent to the shaft 14. Additionally, the excision elements 420 may be connected at their ends by wires, or other flexible connection. This connection can be manipulated to induce the contraction of the excision elements 420 towards shaft 14, to facilitate cutting of the tissue portion adjacent to the shaft 14.

It should be understood that in all the above-exemplified embodiments the device may be rotated, manually or mechanically, to assist in complete tissue treatment (e.g. cutting and removal).

As described above, the invention provides convenient (user-friendly) manner of presentation of the measurement results on a GUI. The use of an array/matrix of tissue characterization sensors defines the array/matrix of measurement locations corresponding to a given position of the probe. The present invention further takes an advantage of such configuration of the probe for presenting/displaying the array/matrix of the measurement locations/sensors together with the corresponding measured data.

Turning now to FIGS. 7 to 13, several examples of a GUI 700 are shown where information collected by the medical device of the present invention is displayed in real-time.

Figure 7:
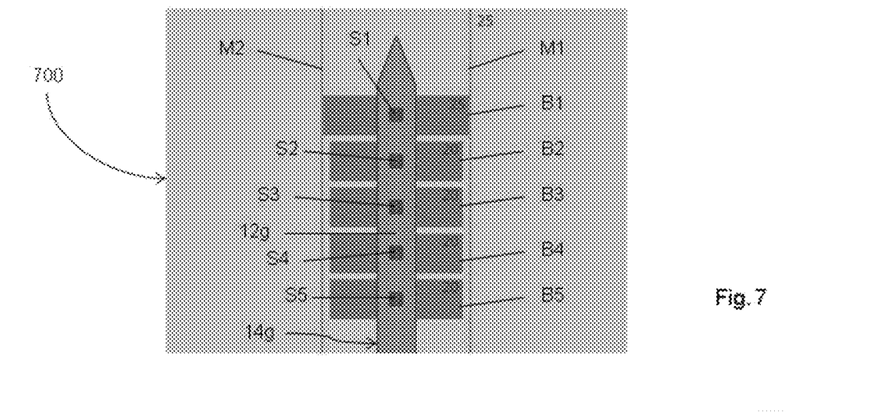
FIGS. 7 to 14 illustrate several examples, respectively, for some features of a graphical user interface (GUI) utilized to present information collected by the sensors of the device of the present invention.

FIG. 7 shows the GUI 700 that graphically illustrates an array 14g of sensors' positions along an axis 12g corresponding to that of the carrier in the tissue characterization probe. In this example, five sensors are considered being illustrated by the sensors' positions S1-S5. Also displayed is the measured data in the form of a corresponding array of data pieces, which in the present example include values corresponding to certain measured parameter/tissue property. As shown, measured data from sensors S2-S5 is presented by value "20", while that of sensor S1 shows higher value "25" of the same measured parameter. Two longitudinal border/limit lines M1 and M2 present maximal/minimal values (threshold) or desired values of the specific parameter being displayed. The border lines values may be user set, through the control unit 19, for each parameter displayed. Moreover, the measured data pieces are presented by bars B1-B5 where the sizes of the bars correspond to differences in the values. Accordingly, in this example, bars (generally, figures) B2-B5 are of the same size and bar B1 is larger. Further, in the present example, the measured data pieces are presented by colorful bars B1-B5 identically placed on the right and left sides of the sensors (i.e. graphical presentation of the sensors' positions). Each bar displays the value corresponding to the tissue parameter of interest measured by the corresponding sensor, i.e. at the corresponding tissue site.

The two longitudinal border/limit lines M1 and M2 may also present dynamically the maximal/minimal value of measured data during a given measurement session (the probe is scanned/moved within the tissue). The maximal/minimal value of measured data is the global value, i.e. taking into account measured data from all the sensors and taking into account the cumulative measured data during the measurement session. In this case, the values (location on GUI) of limit lines M1 and M2 are updated in real-time as different measurement values are obtained, as the probe is scanned/moved within the tissue. At a given time, the values (location on GUI) of limit lines M1 and M2 present the maximal/minimal value of measured data obtained from the beginning of the measurement session up until the current time. The limit lines values may be reset by the user (or automatically based on pre-specified conditions) during the measurement session, through the control unit 19, for each parameter displayed. In this case, the values of limit lines M1 and M2 present the maximal/minimal value of measured data obtained from the time the values were reset up until the current time.

Thus, a change in the bar geometry or shape or size (height/length) may correspond to a change in the value of the tissue parameter being measured, and the measured value may also be presented numerically on each bar. The values of the parameter, and accordingly the bars lengths (sizes), change in real time whenever the device is moved from point to point inside the tissue (i.e. during scanning). In the present example, all the bars B1-B5 are of the same color. Generally, the same color may be used to indicate that all the measured data pieces correspond to the same tissue parameter and/or to the condition that the measured parameter values are at the same side with respect to the predefined threshold.

In some embodiments, the bars may exist on one side only of the measurement axis 12g. In other cases, the same or different measured parameters may be displayed simultaneously at both sides of the measurement axis 12g.

In order to simplify the illustration and understanding, all the FIGS. 7 to 13 exemplify measurements taken by the same number of 5 sensors arranged along the measurement axis, and accordingly the same reference numbers are used throughout all these figures. Every bar/measured data piece is associated with one sensor location. At times, more than one bar may be displayed in association with the same sensor, in which case the bars are usually in different colors, to provide information about more than one parameter/condition simultaneously.

As described above, the sensors may be configured to measure several tissue parameters, such as conductivity, permittivity, impedance, optical property, mechanical property, temperature and others. The bars B1-B5 and/or values on the display correspond to the strength or intensity of the measured parameter. The values usually correspond to properly normalized parameter and are thus non-dimensional (relative units).

As also described above and will be more specifically exemplified in the figures below, the bars may be presented in different colors to indicate either special (exceptional) values of the same parameter, or different parameters presented simultaneously at different sensor/bar couples. The bar color and/or size together with the border lines may be exploited to indicate a range of values. Further, the GUI 700 may include an indication about the mean value of some or all of the measured parameters by lighting up a specific region on the GUI.

Figure 8:
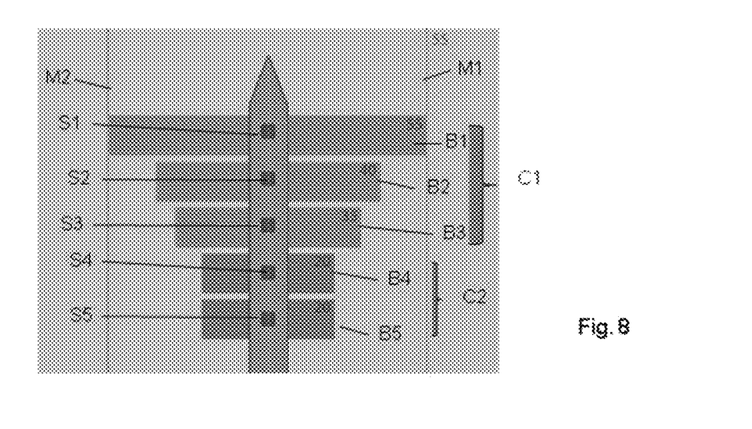

FIG. 8 illustrates an example in which bars B1-B3 have different colors and sizes: bars B1-B3 are of first color C1 (Orange) and different sizes corresponding to values 55, 40 and 35 respectively, while B4 and B5 are of the same size each with the value 20 and are displayed in second color C2 (Blue). In this example, the values of border lines M1 and M2, indicating a maximal value of the measured parameter, are located at value 55 (which coincides with the value of bar B1), while a range of values corresponding to the measured parameter indicative of abnormal tissue property is considered to be between 30-55. Thus, the size and color of bars B1-B3 provide immediate indication of the abnormal condition of the tissue. It should, however, be understood that a different color of bars may be used to indicate measurements of another tissue property.

Figure 9:
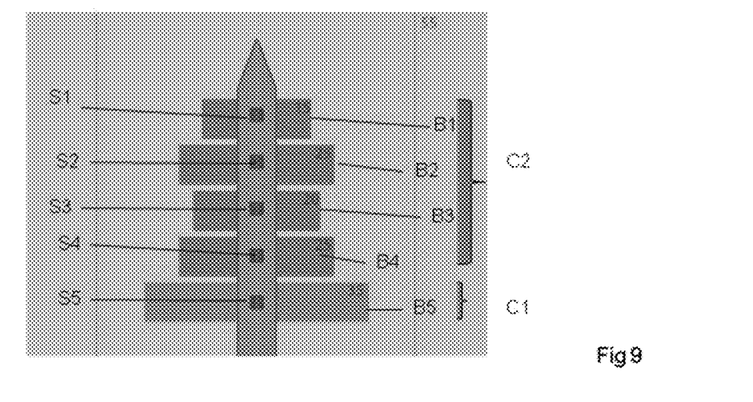

Another similar example, where the bar color and size together with the border lines are used to indicate a range of values is illustrated in FIG. 9. If the measured parameter at a specific location is higher than a minimal value, the corresponding bar has a different color, while the border lines indicate the maximal value of the range, or the maximal value obtained during the measurement session up until the current time. In this example, the minimal value is set to be 30, and the maximal one is at 55. As shown in the figure, each of the measured locations (sensors' position) S1 to S4 shows a different value lower than a minimum one, and accordingly the respective bars B1 to B4 are displayed with different sizes but all of the same second color C2 (Blue). The measured data piece at the sensor's position S5 has a value higher than minimum, and its respective bar B5 has a larger size and a first color C1 (Orange). On the other side, all the bars show values lower than the maximum value 55 presented by the border lines M1 and M2.

Figure 10:
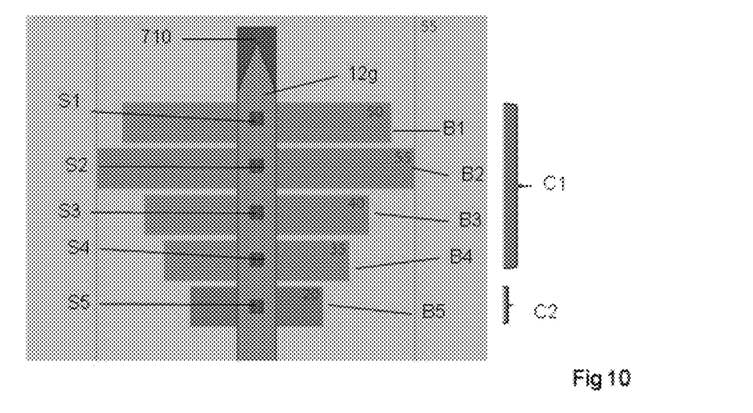

As exemplified in FIG. 10, if the number of measured data pieces (bars) corresponding to high/low values with respect to a predefined threshold and/or the mean value of the measured data pieces exceeds or does not exceed a certain value, then a specific indicator (e.g. color indicator) 710 is displayed indicating the condition that the tissue property at a specific tissue site is higher/lower than a predetermined threshold predefined for the specific parameter. The use of such additional indicator provides additional indications to the operator in real-time. The specific color of the indicator (red color in the present example) may indicate a "problematic" value whether being higher or lower than a normal one, and another color of the indicator (or absence of any such indicator) may indicate that the measured parameter is in the safe range. FIG. 10 may exemplify the condition that the mean value of the measured data pieces is higher than a maximal threshold, even though not all the corresponding data pieces have reached the maximum 55 represented by the border lines. The value of each measured data piece concerns localized information while sometimes the operator is interested in more global information relating to a tissue site and not only to a concrete point in the tissue.

Figure 11:
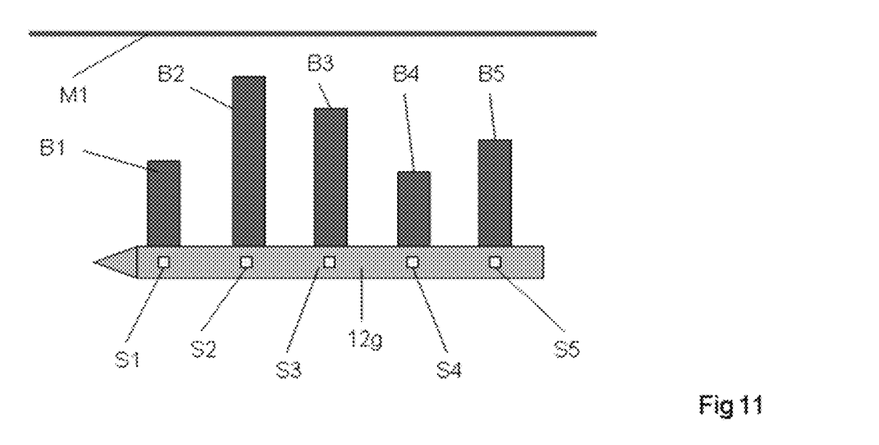

As exemplified in FIG. 11, the GUI 700 may be designed to present a profile of the measured data pieces with respect to a predefined threshold M1 only by the sizes of the bars, and the bars may be only at one side of the measurement axis 12.

Figure 12:
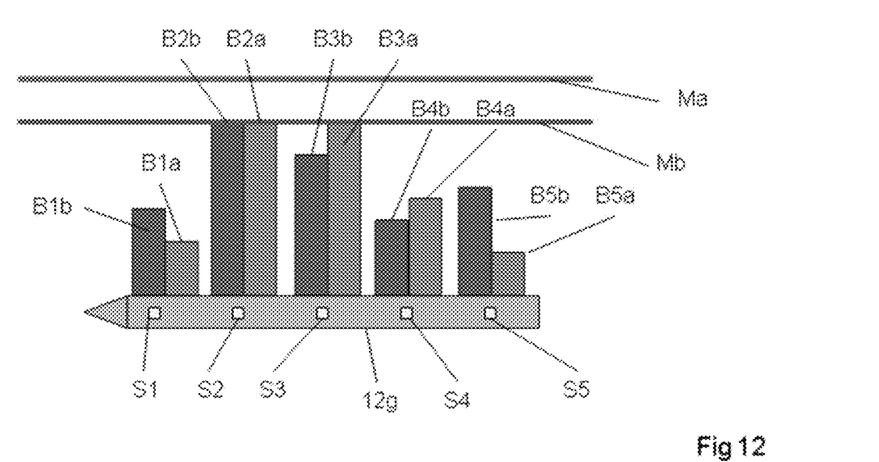

Further, the GUI 700 may be used to display more than one parameter at the same time for each sensor as can be seen in the example of FIG. 12. FIG. 12 shows, for example, a pair of bars associated with each one of the sensors' positions S1-S5. Each bar indicates the value of relevant parameter chosen by the operator. The two bars in the pair may be distinguished by their colors, for example first color (Orange) and second color (Blue). Also, the parameters have their corresponding thresholds presented by respective border lines Ma and Mb.

Figure 13:
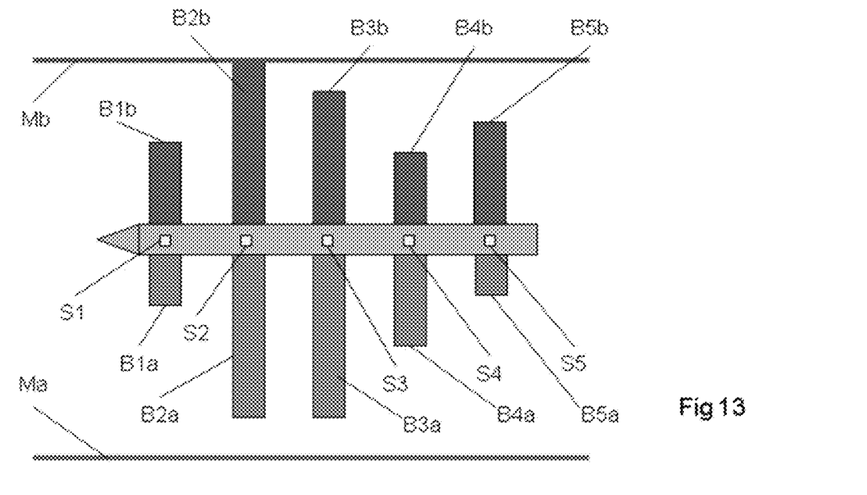

The GUI of the present invention may be configured for displaying different parameters simultaneously at both sides of the measurement axis 12g. This is illustrated in FIG. 13. It should be noted that the GUI may also be configured to combine the feature of FIG. 12 with the feature of FIG. 13 to give information about 4 parameters at once, two at each side of the measurement axis 12g. In the same way, the GUI may display any useful number of parameters concurrently, whether odd or even number. The only limitations on the number of parameters displayed simultaneously would be the overall size/area of the interface and the convenience and readability of the displayed information.

Figure 14:
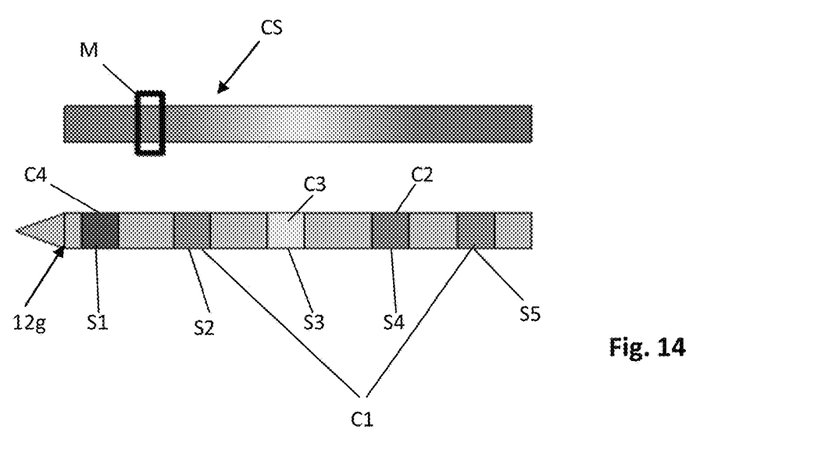

The GUI of the present invention may be configured for displaying the different measured data in the form of different colors, according to a predetermined color scheme, without assigning a bar presentation. This is illustrated in FIG. 14. In this case, the color scheme CS may be presented on the GUI as well. The limit value(s) are captured by an indicator M on the color scheme. As shown in the figure, the measurement locations/sensors' positions are presented by GUI as an array of spaced-apart colored regions, where different colors correspond to different values of the measured data. The sensors S2 and S5 show the same measured data, different from that of the other sensors S1, S3 and S4, and accordingly, the corresponding regions/locations on the display are presented by the first color C1 (Orange) different from other colors. The sensors S1, S3 and S4 show different measured data and accordingly the corresponding locations on the display are colored by different colors C4, C3 and C2 (red, yellow and blue respectively). The displayed colored sensing positions together with the color scheme CS with the indicator M provide immediate information of the profile of tissue property along the measurement axis showing that at sensing positions S1, S2 and S5 the tissue property is close to the threshold.

The graphical presentation of the information from the measured data, as presented in the examples related to FIGS. 7-14, can also be overlaid/merged with imaging data information obtained from other modalities. For example, the information may be merged with Ultrasound, X-ray, or PET (Positron Emission Tomography) image used to guide the probe to specific regions of the tissue. The visibility of the probe on the other imaging modalities is used to identify the location of the sensors on the merged image.

Thus, the present invention provides a novel medical device capable of precisely locating a tissue volume to be treated (removed), and also provides for treating (removing) the tissue by an integral medical device. The invention also provides for displaying the measured data in a manner providing immediate and clear indication of the profile of the tissue parameter(s) being measured.

The invention claimed is:

1. A medical device for use in tissue characterization and treatment, the device comprising: a tissue characterization probe and a control unit integrated with or connectable to the tissue characterization probe; the tissue characterization probe comprising an elongated carrier carrying an array of tissue characterization sensors arranged in a predetermined spaced-apart relationship at least along an axis of said carrier, such that a given position of the probe with respect to a tissue mass provides measurement and analysis of tissue profile of one or more tissue parameters in the tissue mass aligned with said axis of the carrier, and progression of the probe through the tissue mass provides monitoring changes in said tissue profile enabling locating and determining a dimension of an abnormal tissue inside said tissue mass; the control unit comprising a graphical user interface preprogrammed to dynamically display said tissue profile in real-time;

wherein at each given position of the probe,
said array of tissue characterization sensors is preprogrammed to generate a matching corresponding array of tissue characterization signals, each tissue characterization signal originating from a tissue point at a concrete location of each sensor in the array,
said control unit is preprogrammed to analyze said array of tissue characterization signals and generate at least one corresponding array of measured data values of a tissue parameter in response to the analysis,
said tissue profile comprises said at least one array of measured data values of a tissue parameter,
said one or more tissue parameters comprise one or more of a tissue type or a physical tissue property, and
said graphical user interface being preprogrammed to display said at least one array of measured data values of a tissue parameter alongside an array of measurement locations corresponding to said array of sensors, each measured data value being represented by a respective figure having a geometry or size corresponding to the value of the measured data of the tissue parameter, an array of the figures defining the profile of the tissue parameter within a region aligned with the array of sensors.

2. A device according to claim 1, wherein said elongated carrier carries a treatment tool.

3. A device according to claim 2, wherein said treatment tool comprises at least one tissue treating portion, said treatment tool is configured and operable to be selectively shiftable between an inoperative position in which the treatment tool being located substantially entirely inside the carrier and an operative position in which the treatment tool projecting by said at least one tissue treating portion towards outside the carrier.

4. A device according to claim 3, wherein said treatment tool is configured and operable with a variable dimension of said at least one tissue treating portion projectable from the carrier.

5. A device according to claim 3, wherein the tissue treating portion of the treatment tool is movable with respect to the carrier along said axis.

6. A device according to claim 3, wherein the treatment tool is configured for carrying out at least one of the following: biopsy, cutting, delivering physical treatment, delivering treatment medication, diagnostics.

7. A device according to claim 3, wherein the tissue treating portion is configured as a tissue excision element.

8. A device according to claim 7, wherein the at least one excision element comprises a tissue collecting unit for collecting tissue being removed.

9. A device according to claim 7, wherein the treatment tool comprises a body and at least one excision element projectable from said body.

10. A device according to claim 9, wherein the carrier is formed with slot interspaced between the tissue characterization sensors, such that at each location along the carrier there are at least two peripheral slots.

11. A medical device of claim 1, wherein the figures are in the form of bars.

12. A medical device according to claim 1, wherein said graphical user interface is preprogrammed to display alongside each figure indicative of each measured value a respective numerical value corresponding to the measured data value of the tissue parameter being sensed by the respective sensor, an array of the numerical values defining the profile of the measured tissue parameter within a region aligned with the array of sensors.

13. A medical device according to claim 1, wherein said figures are colored, such that the figures corresponding to the same measured data have the same color and figures corresponding to different measured data have different colors.

14. A medical device according to claim 1, wherein said graphical user interface is preprogrammed to display data indicative of a global value for the tissue parameter being measured.

15. A medical device according to claim 1, wherein said graphical user interface is preprogrammed to display said array of measurement locations in the form of the array of measured data each being represented by a colored region, such that the regions corresponding to the same measured data have the same color and regions corresponding to different measured data have different colors.

16. A medical device according to claim 15, wherein said graphical user interface is configured and operable to display data indicative of a threshold value for the tissue property being measured.

17. A medical device according to claim 1, wherein said control unit is preprogrammed to receive from one or more imaging modalities imaging data of the tissue characterization probe position with respect to tissue being measured, and to merge the imaging data with the measured data values, to thereby identify locations of the sensors on a merged image.

18. A control unit for monitoring measurements of tissue properties, the control unit being preprogrammed to receive an array of tissue characterization signals produced by an array of sensors arranged in a predetermined spaced-apart relationship along a measurement axis, each tissue characterization signal originating from a tissue point at a concrete location of each sensor in the array, the control unit being preprogrammed to analyze said array of tissue characterization signals and generate at least one corresponding array of measured data values of a tissue property, the control unit comprising a graphical user interface preprogrammed to present information in the form of an array of locations spaced-apart along an axis corresponding to the array of said sensors, and said at least one array of measured data values of a tissue property in association with said array of locations, each of the measured data values being represented by a respective figure having a geometry or size corresponding to the measured data value of a tissue property being sensed by the respective sensor, an array of the figures defining the profile of the measured tissue property within a region aligned with the array of sensors, thereby providing an operator with information regarding a measured tissue profile along a tissue mass aligned with the array of sensors.

19. A control unit according to claim 18, wherein the graphical user interface is preprogrammed to display alongside each figure indicative of each of the measured data values being a respective numerical value corresponding to the measured data value of a tissue property being sensed by the respective sensor, an array of the numerical values defining the profile of the measured tissue property within a region aligned with the array of sensors.

20. A control unit according to claim 19, wherein said figures are colored, such that the figures corresponding to the same measured data have the same color and figures corresponding to different measured data have different colors.

21. A control unit according to claim 18, wherein said graphical user interface is preprogrammed to display data indicative of a global value for the tissue property being measured.

22. A control unit according to claim 18, wherein said graphical user interface is preprogrammed to display said array of measurement locations in the form of the array of measured data each being represented by a colored region, such that the regions corresponding to the same measured data have the same color and regions corresponding to different measured data have different colors.

23. A control unit according to claim 22, wherein said graphical user interface is configured and operable to display data indicative of a threshold value for the tissue property being measured.

24. A control unit according to claim 18, preprogrammed to receive from one or more imaging modalities imaging data of a position of a tissue characterization probe carrying the array of sensors with respect to tissue being measured, and to merge the imaging data with the measured data values, to thereby identify locations of the sensors on a merged image.

25. A graphical user interface preprogrammed to present information related to tissue characterization signals received from an array of sensors arranged in a predetermined spaced-apart relationship along a measurement axis, each tissue characterization signal originating from a concrete location of each sensor in the array, the presented information being in the form of an array of locations spaced-apart along an axis corresponding to the array of said sensors, and a corresponding array of measured data values in association with the array of said locations, said array of measured data values being indicative of said tissue characterization signals and being presented by one of the following: (1) a respective figure having a geometry or size corresponding to the measured data value of a tissue property being sensed by the respective sensor, an array of the figures defining the profile of the measured tissue property within a region aligned with the array of sensors; (2) respective figure and numerical value, a geometry or size of the figure and the numerical value corresponding to the measured data value of a tissue property being sensed by the respective sensor, an array of the figures and numerical values defining the profile of the measured tissue property within a region aligned with the array of sensors.

\* \* \* \* \*